United States Patent [19]

Isliker et al.

[11] Patent Number: 5,089,602

[45] Date of Patent: Feb. 18, 1992

[54] PROCESS FOR THE MANUFACTURE OF APOLIPOPROTEINS FROM HUMAN BLOOD PLASMA OR SERUM

[75] Inventors: Henri Isliker, Lausanne, Switzerland; Manuel C. Peitsch, Frederick, Md.; Hans J. Heiniger; Peter G. Lerch, both of Bern, Switzerland; Jean J. Morgenthaler, Boll, Switzerland

[73] Assignee: Rotkreuzstiftung Zentrallaboratorium Blutspendedienst SRK, Bern, Switzerland

[21] Appl. No.: 670,473

[22] Filed: Mar. 11, 1991

Related U.S. Application Data

[63] Continuation of Ser. No. 307,289, Feb. 7, 1989, abandoned.

[30] Foreign Application Priority Data

Feb. 8, 1988 [CH] Switzerland .............................. 431/88

[51] Int. Cl.$^5$ .......................... C07K 3/02; C07K 3/12; A61K 35/6; A61K 37/00

[52] U.S. Cl. ....................................................... 530/359
[58] Field of Search .......................... 530/359; 514/21

[56] References Cited

FOREIGN PATENT DOCUMENTS 61-53222  3/1986  Japan .

OTHER PUBLICATIONS

Mezdour et al. J. of Chromatography, 414 (1987) 35–45.

*Primary Examiner*—John Doll
*Assistant Examiner*—Choon P. Koh
*Attorney, Agent, or Firm*—Wenderoth, Lind & Ponack

[57] ABSTRACT

Apolipoproteins are isolated from human blood plasma fractions which contain apolipoproteins by suspending these fractions in buffer solutions. The suspensions are subsequently incubated with a lower aliphatic alcohol, either with or without an organic solvent. The phase which contains the lipoproteins is separated and concentrated. The products obtained according to the procedure may be used primarily for the treatment of cardiovascular diseases, in particular hypercholesterolemia.

16 Claims, No Drawings

PROCESS FOR THE MANUFACTURE OF APOLIPOPROTEINS FROM HUMAN BLOOD PLASMA OR SERUM

This application is a continuation of now abandoned application, Ser. No. 07/307,289 filed Feb. 7, 1989 now abandoned.

BACKGROUND OF THE INVENTION

Cardiovascular diseases are very common in industrialized countries; their causes are complex. A number of risk factors which parallel these diseases have, nevertheless, been defined. If an individual has one or even several of these risk factors, he/she has an increased risk for cardiovascular diseases. Among these factors are: increased blood pressure; smoking (particularly cigarettes); obesity; hypercholesterolemia; male sex; diabetes; history of cardiovascular diseases in the family.

Some risks are unavoidable; others may be influenced by changes in behavior; a third group finally may be modified by drugs. Elevated levels of cholesterol in the blood belong to the third group. A distinction has to be made between two different components, which both contain cholesterol: the so-called low density lipoproteins (LDL) and the high density lipoproteins (HDL). Elevated cholesterol levels in the LDL-fraction increase the risk of cardiovascular diseases ('bad cholesterol'), while elevated cholesterol levels in the HDL-fraction decrease the risk of cardiovascular diseases ('good cholesterol').

Besides the already mentioned HDL and LDL blood also contains chylomicrons, very low density lipoproteins (VLDL), and intermediate density lipoproteins (IDL). HDL may be subdivided into the groups $HDL_1$, $HDL_2$, and $HDL_3$. The distinction of groups and subgroups is based on different physicochemical (e.g., density, composition, morphology) and functional properties.

Drugs that lower the total concentration of cholesterol in blood have been described; there are even pharmaceuticals available which specifically lower the concentration of LDL-cholesterol while simultaneously increasing HDL-cholesterol. These therapies are based on a number of different mechanisms: on one hand, resorption of lipids in the gut may be reduced; on the other hand, it is also possible to inhibit a key enzyme of cholesterol biosynthesis (hydroxymethylglutaryl-CoA-reductase; HMG-CoA-reductase), thus lowering the synthetic rate of cholesterol. However, all these drugs (Colestipol, nicotinic acid, Lovastatin etc.) have to be taken over a long time and side-reactions cannot be excluded.

HDL are complex entities, composed of lipids (e.g., phosphatidyl choline, sphingomyelin, cholesterol and cholesteryl esters) and proteins (apoproteins; e.g., apoA-I, apoA-II, apoE). The individual components are held together by non-covalent bonds. HDL particles are continuously metabolized; they fall apart and are being rebuilt from new components, which are in turn synthesized in various organs. Another possibility to influence the ratio of LDL- to HDL-cholesterol in favor of the 'good cholesterol' is therefore the addition of an excess of the protein(s) present in HDL; this will cause more cholesterol to be incorporated into HDL.

Apolipoproteins have already been isolated from HDL by conventional methods and used for substitution therapy in cases of familial an-alpha-lipoproteinemia (Tangier disease).

The traditional method for isolating HDL consists of a series of ultracentrifugation steps at various densities [Brewer et al., Methods in Enzymology 128; J. P. Segrest, J. J. Albers, edts.; Academic Press, Orlando, Fla., U.S.A., 1986]. Plasma or serum was brought to a predetermined density by the addition of solid potassium bromide; the solution was then subjected to ultracentrifugation. The upper layer was removed and more potassium bromide (solid or in concentrated solution) was added to the lower phase, which was again ultracentrifuged. With this method, lipoproteins of increasing density could be isolated sequentially.

This method is, however, completely unsuitable for industrial use, since the capacity of currently available ultracentrifuges does not exceed approximately 400 mL. The tedious method described above therefore does not yield more than a few hundred mg of protein per run. As an additional disadvantage, the plasma used is unsuitable for conventional fractionation processes described below because of its high content of potassium bromide.

According to AT-B-380 167, lipoproteins from human serum may be separated and also analyzed by sequential precipitation with polyethylene glycol. Depending on the polyethylene glycol concentration and the pH-value of the medium, either the VLDL and LDL were found in the precipitate and the $HDL_2$ and $HDL_3$ in the supernatant, or the VLDL, LDL, and $HDL_2$ were in the precipitate and the $HDL_3$ in the supernatant.

Fractions prepared according to this method, precipitates as well as supernatants, are contaminated with polyethylene glycol, which is difficult to remove from the desired proteins.

According to an earlier procedure described in FR 2 343 251, lipoproteins were separated from other blood or plasma proteins by ion exchange chromatography with a cation exchanger. Under suitable conditions, the VLDL and the LDL bound to the ion exchanger, while HDL passed the column unretarded. VLDL and LDL were eluted and recovered from the column by changing the buffer solution. The HDL could also be bound and eluted by using another cation exchanger.

LDL- and HDL-apolipoproteins, which are soluble in urea, could also be separated into individual components by chromatography with anion exchangers [H. Mezdour et al., J. Chromatogr. 414, 35-45, 1987]. The FPLC (fast protein liquid chromatography) equipment, produced by Pharmacia, Uppsala, Sweden, fitted with a Mono Q column, was particularly well suited for this purpose. The separation may then be achieved within 30 minutes. In order to obtain a sufficient purity a second isolation step is, however, required.

Chromatographic procedures for the separation of proteins are very common on a laboratory scale; they are often less suited for industrial scale processing, because they are either too expensive and/or suitable for only small amounts of material. Additionally, the solutions have to be adjusted to a protein concentration of about 2% before processing; in the case of plasma proteins, the starting material has therefore to be diluted. The diluted plasma may not be processed any longer by the procedures mentioned in the next paragraph.

Human blood plasma is nowadays collected in large amounts and processed to individual fractions; some of these fractions contain the lipoproteins. The fractions may be produced by ethanol fractionation according to a procedure originally developed in the United States and known as Cohn-Oncley-method [E. J. Cohn et al., J. Am. Chem. Soc. 68, 459–475, 1946; J. L. Oncley et al., J. Am. Chem. Soc. 71, 541–550, 1949]. Plasma fractions containing lipoproteins may also be produced by a variant of this method, the Kistler-Nitschmann procedure [H. Nitschmann et al., Helv. Chim. Acta 37, 866–873, 1954; P. Kistler and H. Nitschmann, Vox Sang 7, 414–424, 1962].

DETAILED DESCRIPTION OF THE INVENTION

The apolipoproteins may now be prepared from the fractions of the ethanol precipitation process according to a much simpler method. This new method may easily be integrated into the existing fractionation schemes, since fractions that were hitherto discarded are used as starting material.

According to the present invention, apolipoproteins are prepared from fractions of human blood plasma or serum by resuspending said fractions in an aqueous buffer solution in the pH-range 3 to 5 or 6 to 9. Undesirable contaminants are precipitated by addition of a short chain aliphatic alcohol (e.g., methanol, ethanol, propanol, or isopropanol; preferably ethanol). The phase which contains the lipoproteins is separated and the lipoproteins contained in it are concentrated. Should aggregates of lipoproteins form, e.g., as a consequence of precipitation induced by the concentration step, these aggregates may be disaggregated by dissolving the product at elevated temperature, at a slightly alkaline pH, or by the addition of chaotropic agents or surface-active substances.

The starting material is resuspended in an aqueous buffer solution with a pH-value preferably between 3 and 5 or between 6 and 9. Possible examples of buffer substances include $NaHCO_3$, $Na_2B_4O_7$, $Na_2HPO_4$, sodium citrate, or Tris, after proper adjustment of the pH-value. These substances are used in a concentration range of 5 mM to 2M. Dissolution and/or extraction may be aided by including chaotropic agents in the buffer, e.g., urea, guanidine hydrochloride, or an inorganic, watersoluble thiocyanate like ammonium thiocyanate; in this case, extraction of the apolipoproteins is possible in the pH-range from 3 to 9.

Chaotropic agents may be replaced by surface-active substances, e.g., polysorbates like polyoxyethylen-(20)-sorbitan-monolaurate, -monopalmitate, -monostearate, or monooleate (Polysorbate 20, 40, 60, and 80, or the corresponding products known as Tween®-20, -40, -60, and -80 produced by ICI America Inc, Atlas Chemicals Division, Wilmington, Del., USA), an octylphenoxy polyethoxyethanol (Triton®X-45, X-100, or X-114 of Rohm and Haas Co., Philadelphia, Pa., USA), or a polyethylene glycol (e.g., PEG 4000).

Solubility may also be improved by adding water-soluble salts like sodium chloride in a concentration of up to 5M.

Extraction of the apolipoproteins may also be carried out in the presence of a preferably non-polar organic solvent, e.g., chloroform, dichloromethane, hexane, or benzene; the apolipoproteins are then found in the aqueous phase.

The phase which contains the apolipoproteins after suspension of the starting material is separated from the other phases, which are discarded. Separation may be achieved by filtration, centrifugation, or decantation. The phase which contains the apolipoproteins is identified by suitable analytical methods, e.g., by polyacrylamide gel electrophoresis.

Undesirable contaminants may be eliminated by adding, preferably in the cold, a short-chain aliphatic alcohol (e.g., methanol, ethanol, propanol, isopropanol; preferably ethanol) to the separated phase. After incubation the precipitate may be removed, preferably by filtration or centrifugation. The supernatant may be further processed for removal of ethanol or other contaminants by the methods described below.

Extraction of the apolipoproteins with the aqueous buffer solution and precipitation of undesirable contaminants with a short-chain, aliphatic alcohol may be carried out simultaneously, in one processing step.

In the latter case, the already mentioned, non-polar organic solvent may also be added simultaneously. A multi-phase system then forms, of which the aqueous phase is separated again and incubated once more with the short-chain, aliphatic alcohol.

Purification of apolipoproteins in the supernatants may be carried out in various ways. A first possibility is to dialyze the supernatant against an aqueous buffer solution in the pH-range 3 to 5 or 6 to 9; apolipoproteins remain in solution, while contaminants are largely precipitated and can be removed by filtration or centrifugation.

According to a different method, an aqueous buffer solution (e.g., 10 mM sodium phosphate, pH 8, 150 mM NaCl) with a pH-value of around 8 is added to the supernatant. The precipitate formed is discarded, the supernatant contains the apolipoproteins which may be further processed.

Apolipoproteins may be concentrated from solutions that contain them by various methods, e.g., membrane filtration or lyophilization. They may also be precipitated by adjusting the pH-value to 5 to 6 and/or the concentration of sodium chloride or another water-soluble salt to 0.1 to 0.2 moles/L. Alternatively, the apolipoproteins may be concentrated by precipitation with ethanol at a concentration of up to 80%, addition of polymers like polyvinylpyrrolidone or dextran sulfate, or they may be concentrated by adsorption onto an ion exchanger, e.g., the anion exchanger DEAE-Trisacryl LS, followed by subsequent elution in high concentration by increasing the ionic strength with a water-soluble salt, e.g., $NH_4HCO_3$.

Lipids may be removed at any step of the procedure by treating the product with a preferably non-polar organic solvent, e.g., an aliphatic hydrocarbon like hexane, an aliphatic halogenated hydrocarbon like chloroform or dichloromethane, an ether like diethylether or dibutylether, or a mixture of these solvents. Removal of lipids may in particular be done in the beginning of the procedure, simultaneously with the suspension in an aqueous buffer, or at the very end of the procedure, with lyophilized product.

Solubilization of the precipitated apolipoproteins and production of a material free of aggregates may be achieved by adding chaotropic substances like guanidine hydrochloride or urea, ionic or non-ionic detergents, or combinations thereof; these substances are subsequently removed with a suitable method, e.g., dialysis, diafiltration, adsorption, or gel filtration. Alternatively, solubilization may be carried out in a slightly basic buffer, e.g., Tris, phosphate, or carbonate at temperatures of up to 70° C. The quality of the product with respect to stability, sterility, and viral safety may be improved by pasteurization, which is done preferably in the final container in the presence of stabilizers like carbohydrates (e.g., sucrose or mannitol).

For use in human medicine the apolipoproteins have to be formulated in a galenically acceptable form. An aqueous solution of apolipoproteins, prepared according to the present invention, with or without the addition of accepted buffer substances like sodium phosphate, carbonate, or citrate in a physiological pH-range, may be acceptable. The solution may also be lyophilized and redissolved before use in a suitable solvent (water, buffer solution, salt solution, e.g., NaCl). It is also possible to prepare for medical use proteoliposomes which contain apolipoproteins and lipids (phospholipids like lecithin, alone or together with other lipids like cholesterol).

Starting from precipitate B of the Kistler-Nitschmann process, up to 70% of the apolipoprotein A-I contained in it were recovered. With precipitate IV, recoveries of up to 50% were reached, with a purity of 90 to 95%. HDL contains mostly the apolipoproteins A-I, A-II, and A-IV; during the fractionation process according to Kistler and Nitschmann approximately 40% of the apolipoprotein A-I contained in the starting plasma are found in each of precipitate B and of precipitate IV.

Purities and recoveries were evaluated by SDS polyacrylamide gel electrophoresis and with protein assays ($A_{280\ nm}$, Folin, and BioRad protein assay, BioRad Laboratories, Munich, FRG).

Apolipoproteins, in particular apolipoprotein A-I (apoA-I), are activators of the enzyme lecithin-cholesterol-acyltransferase (LCAT), which occurs in human blood. Apolipoproteins prepared according to this invention contain mostly apoA-I and strongly activate LCAT. In vitro assays of this activity may be carried out with $^{14}C$-labelled cholesterol, which is transformed into cholesteryl esters in the presence of lecithin and apolipoproteins. Cholesteryl esters and cholesterol may be separated analytically by thin layer chromatography.

The importance of the presently disclosed invention rests on the fact that apolipoproteins may now be recovered from plasma fractions which were so far useless and discarded, and also on the observation that these products keep their biological activity after storage.

Apolipoproteins prepared according to the present method may be used for the prophylaxis and therapy of cardiovascular diseases or for the manufacture of pharmaceutical preparations used for this purpose. They are in particular suitable for the treatment-either prophylactic or therapeutic-of any type and any manifestation of hypercholesterolemia. They may be used as the only active ingredient or in combination with activators of the lecithin cholesterol acyl transferase (LCAT) and its substrates, particularly lecithin. Additionally, they may be used as a substitution therapy in conjunction with LDL apheresis and in combination with inhibitors of the hydroxymethyl-glutaryl-CoA-reductase. They may also be used postoperatively as a prophylactic infusion after heart transplant, triple bypass, and other heart operations.

Pharmaceutical preparations which contain apolipoproteins prepared according to the present method, together with the usual carrier substances and excipients, are therefore another subject of the present invention. These pharmaceutical preparations may be used for the prophylactic or therapeutic treatment of cardiovascular diseases, particularly hypercholesterolemia and for other indications as mentioned above.

Administration of the apolipoproteins for the indications mentioned above shall be by the intravenous route, either by injection or by infusion, or by the peroral or anal route. The recommended dose for adult human beings shall be in the range 1 mg to 1 g/(kg body weight $\times$ day).

EXAMPLE 1

0.5 g of centrifuged precipitate B [Kistler-Nitschmann procedure] were resuspended in 1 mL buffer (10 mM Tris/HCl [tris(hydroxymethyl)-aminomethane hydrochloride], pH 8.0, 6M urea); after the addition of 1 mL chloroform/ethanol (1:1 v/v) the mixture was vigorously shaken and incubated for 1 hour at 0° C. The suspension was subsequently centrifuged for 10 minutes at 10,000$\times$g and at 0° C. The lower and intermediate phases were discarded. 0.7 mL absolute ethanol were added for each mL of supernatant and incubation at 0° C. was continued for 1 hour. The supernatant recovered by another centrifugation (same conditions as above) was dialyzed against phosphate buffer (20 mM $Na_2HPO_4$, pH 7.4, 150 mM NaCl) and lyophilized.

Essentially the same procedure was also applied to filtered precipitate B; the concentration of Tris in the extraction buffer was raised to 110 mM. Identical results were obtained when chloroform was replaced by dichloromethane.

Preparation of precipitate B: pooled, venous human plasma was adjusted to pH 5.8 with 4.8M sodium acetate buffer of pH 4.0; ethanol concentration was brought to 19% and the temperature was lowered concomitantly from 0° C. to $-5.5°$ C. The ensuing suspension was filtered and the supernatant a used for the preparation of precipitate IV. The precipitate (precipitate A) was resuspended in water at 0° C. (2% protein concentration) and the pH adjusted to 4.8 with a mixture of 1 volume of 50 mM $Na_2HPO_4$ and 6 volumes of 50 mM acetic acid. After 2 hours stirring the pH was adjusted to 5.1 with another buffer (1 vol. 50 mM $Na_2HPO_4$ and 0.833 vol. 50 mM acetic acid); ethanol concentration was increased to 12%, the temperature was concomitantly decreased to $-5°$ C. Precipitate B was obtained by filtration or centrifugation of this suspension. The supernatant was used for the isolation of immunoglobulins.

EXAMPLE 2

5 g of precipitate IV of the Kistler-Nitschmann method were treated with 20 mL of phosphate buffer (20 mM $Na_2HPO_4$, 20 mM NaCl). The pH was adjusted to 7.0 with NaOH and the suspension was incubated for 30 minutes at 0° C. After centrifugation (10 minutes, 0° C., 10,000$\times$g) ethanol was added to the supernatant to a final concentration of 68%. The mixture was again incubated (30 minutes, 0° C.) and centrifuged (10 minutes, 0° C., 10,000$\times$g) and the supernatant was dialyzed against phosphate buffer and lyophilized as described in example 1.

Preparation of precipitate IV: ethanol was added to supernatant a (cf. example 1) to a final concentration of 40% with concomitant decrease of the temperature to $-6°$ C. Precipitate IV was separated from this suspension by centrifugation or filtration; the supernatant was used for the isolation of albumin.

EXAMPLE 3

1 g precipitate B prepared according to the method of Kistler and Nitschmann (filtered with filter aids) was resuspended in 4 mL of buffer (either 6M urea in 10 mM Tris/HCl, pH 8.0, or 6M urea, 20 mM $Na_2HPO_4$, or 4M guanidine hydrochloride, 20 mM $Na_2HPO_4$); the pH of the suspension was adjusted to 8.0±0.2 with 1M NaOH. 4 mL of a mixture of 96% ethanol and dichloromethane (1+1 vol./vol.) or of 96% ethanol and diethylether (1+1 vol./vol.) were added to the suspension, stirred, and incubated for 1 hour at 0° C. The aqueous phase obtained after centrifugation (10 minutes, 0° C., 10,000×g) was mixed with an equal volume of 96% ethanol, incubated for 16 hours at 4° C., and centrifuged again (10 minutes, 0° C., 10,000×g). The supernatant was dialyzed for 5 hours at 4° C. against 0.15M NaCl, then clarified by centrifugation or filtration; it was enriched in apolipoprotein A-I and could be further processed by dialysis or lyophilization.

The variants mentioned or any combinations thereof result in practically the same final product.

EXAMPLE 4

1 g of (filtered) precipitate B was suspended in 4 mL of buffer (6M urea, 10 mM $H_3BO_3$, 10 mM citric acid). The pH was adjusted to 4.0 with 1M NaOH and the suspension stirred for 30 minutes at 20° C. Ethanol was added to a final concentration of 70% to the supernatant obtained by centrifugation (5 minutes, 20° C., 3,000×g) after it had been cooled to 0° C. The mixture was centrifuged (15 minutes, 4° C., 10,000×g) after 1 hour incubation and the supernatant was dialyzed against PBS (10 mM phosphate, pH 7.4, 140 mM NaCl); it contained the purified apolipoprotein.

EXAMPLE 5

1 g of precipitate B was resuspended in 4 mL of buffer (20 mM $Na_2HPO_4$); the pH was adjusted to 8.0 with 1M NaOH. After 30 minutes stirring at 0° C. cold ethanol was slowly added to the filtrate to a final concentration of 68%. The mixture was incubated for 1 hour at 4° C. and then centrifuged (15 minutes, 4° C., 10,000×g); the supernatant, after dialysis for 3 hours against PBS at 4° C. and filtration, contained the purified apolipoprotein.

EXAMPLE 6

To the supernatant of example 5, 0.1 to 1 volume of either water, 10 mM phosphate buffer of pH 8.0, or 10 mM phosphate buffer with up to 2M NaCl were added per unit of volume of supernatant; the mixture was stirred for 30 minutes at 4° C. and centrifuged. The supernatant contained the apolipoprotein, which could be collected by dialysis against a buffer of low ionic strength, followed by lyophilization, or by precipitation with ethanol at a final concentration of up to 78%.

EXAMPLE 7

1 g of precipitate IV obtained by filtration according to the method of Kistler and Nitschmann was resuspended in 4 mL of 20 mM NaCl or in 4 mL of buffer (10 mM $H_3PO_4$, 10 mM $H_3BO_3$, 10 mM citric acid); the pH-value of the NaCl-suspension was brought to 8.15 with 1M NaOH, the pH-value of the buffer suspension to 6.5 to 7.5. After 1 hour stirring at 0° C. ethanol was added to a final concentration of 68%; the supernatant obtained by centrifugation was further processed either by dialysis and/or another ethanol precipitation and lyophilization.

EXAMPLE 8

45 kg of precipitate B were resuspended in 180 L of buffer solution (5 mM $NaHCO_3$, 68% ethanol); the pH was adjusted to 7.2. The suspension was filtered at 2° C. after 3 hours of stirring. The pH of the filtrate was readjusted to 5.1; after incubation overnight at 1° C. a precipitate formed, which was also removed by filtration. This yielded 557 g of wet precipitate, which was delipidated as far as possible with 96% ethanol and subsequently frozen. 100 g of this precipitate were dissolved in 500 mL 4M guanidine hydrochloride, 5 mM sodium phosphate, pH 7.4, and stirred 1 hour at 20° C. The solution was subsequently filtered, diafiltered against 5 mM sodium phosphate buffer, pH 7.4, and brought to a protein concentration of 6%.

EXAMPLE 9

The solution obtained in example 8 was adjusted to a final concentration of 10% sucrose and 5% protein, sterile-filtered and filled into glass bottles which were closed and pasteurized for 10 hours at 60° C.

EXAMPLE 10

The solution obtained in example 8 was adjusted to a final concentration of 10% sucrose or 5% mannitol and 5% protein; it was then pasteurized for 10 hours at 60° C. and 50 mL aliquots were filled under sterile conditions into glass bottles. The contents of the bottles were lyophilized and the bottles were capped. The lyophilized material was dissolved before use in 50 mL of sterile, pyrogen free water.

EXAMPLE 11

100 g of the frozen precipitate of example 8 were dissolved in 500 mL 4M guanidine hydrochloride, 5 mM sodium phosphate, pH 7.4, and stirred 1 hour at 20° C. The solution was then filtered, dialyzed against 20 mM phosphate buffer, pH 7.4, and further processed to liposomes:

a) 7.7 g of lecithin and 11.6 g of cholesterin were dissolved in an organic solvent and the solvent was then evaporated with a stream of nitrogen. The residue was mixed with 10 g of apolipoprotein dissolved in 10 L of phosphate buffer and 930 g of sodium cholate; the mixture was incubated for 30 minutes at 24° C. The liposomes that have formed were separated from the detergent by subsequent dialysis, diafiltration, gel chromatography, or incubation with an adsorbens like BioBeads ® (BioRad, Richmond, Calif., U.S.A.). Cholate could be replaced by other surface-active substances like deoxycholate, Triton ®, Brij ®, Tween ®, 3-[(3-chloramidopropyl)dimethylammonio]-1-propane sulfonate, or octyl-$\beta$-glucoside in appropriate amounts.

b) Lipids dissolved in an organic solvent like ethanol or ether were injected through a fine needle into the protein solution; the solvent was then removed either by one of the methods mentioned in a) or by heating the mixture.

c) A lipid emulsion was added to the protein solution and sonicated with an ultrasound probe or in an ultrasound bath under exclusion of oxygen. Treatment with ultrasound could be combined with freezing and thawing of the mixture.

The products described in a), b), or c) could be used as proteoliposomes or as protein-lipid mixtures in liquid or in lyophilized form.

In the examples 1 to 11, substances may be added to the buffer solutions that protect proteins against oxidation (e.g., 1 mM mercaptoethanol, dithiothreitol, glutathione, or EDTA) or that inhibit protease activity (natural or synthetic protease inhibitors, e.g., soy bean trypsin inhibitor of phenyl methyl sulfonyl fluoride)

Substances may also be added to the final product in order to stabilize it or to increase its biological activity (e.g., lipids like lecithin), and to improve the solubility of the lyophilizate (sugars, e.g., 5 to 10% sucrose or mannitol; 0.1 to 0.5M glycine; 1 to 10 g/L albumin).

These are only examples; people skilled in the art may find other variants without leaving the field of the invention.

We claim:

1. A process of preparing apolipoproteins, which comprises the following steps:
   providing an apolipoprotein-containing fraction resulting from subjecting human blood plasma or serum to an ethanol precipitation process;
   suspending said fraction in an aqueous buffer solution having a pH of 3 to 9 to obtain a suspension;
   adding a lower aliphatic alcohol to said suspension and incubating the resulting mixture to precipitate undesirable contaminants from said mixture and form an apolipoprotein-containing phase;
   separating said apolipoprotein-containing phase from the precipitated contaminants; and
   concentrating the separated apolipoprotein-containing phase to a higher concentration of apolipoproteins to obtain a product which contains mostly apolipoprotein A-I.

2. The process according to claim 1, wherein the pH of the aqueous buffer solution is from 3 to 5.

3. The process according to claim 1, wherein the pH of the aqueous buffer solution is from 6 to 9.

4. The process according to claim 1, wherein the aqueous buffer solution contains a member selected from the group consisting of chaotropic substances, surface-active substances and water-soluble salts.

5. The process according to claim 1, wherein the separation of the apolipoprotein-containing phase from the precipitated contaminants is conducted by means of filtration, centrifugation or decantation.

6. The process according to claim 1, wherein the apolipoprotein is obtained as a precipitate, and the process further comprises dissolving the apolipoprotein precipitate.

7. The process according to claim 1, wherein the suspension in the aqueous buffer solution is first filtered, centrifuged or decanted, before the filtrate or supernatant is incubated with the lower aliphatic alcohol.

8. The process according to claim 1, wherein the incubation with the lower aliphatic alcohol is carried out in the cold.

9. The process according to claim 1, wherein the apolipoprotein containing phase is brought to a higher concentration of apolipoproteins by membrane filtration, lyophilization, precipitation at pH 5 to 6, or by addition of a lower aliphatic alcohol, a water-soluble salt or a polymeric substance, or by adsorption to and elution from a solid carrier material.

10. The process according to claim 6, wherein the apolipoprotein precipitate is dissolved by moderate heating or by adding chaotropic substances, surface-active substances, or a slightly basic buffer solution, said substances then being removed by dialysis, diafiltration, adsorption or gel filtration.

11. The process according to any one of claims 1, 7, 8, 9 or 10, wherein the separated, apolipoprotein-containing phase for further purification is dialyzed against an aqueous buffer solution of pH range 3 to 5 or 6 to 9 before the apolipoproteins are brought to a higher concentration, and the dialyzed solution is recovered.

12. The process according to any one of claims 1, 7, 8, 9 or 10, wherein the separated, apolipoprotein-containing phase for further purification is treated with an aqueous buffer solution of pH about 8 before the apolipoproteins are brought to a higher concentration, the thus formed precipitate is discarded and the liquid phase is recovered.

13. The process according to any one of claims 1, 7, 8, 9 or 10, wherein the suspension in the aqueous buffer solution is incubated with the lower aliphatic alcohol in admixture with a non-polar organic solvent, thereby causing the formation of a multi-phase system from which the aqueous phase is separated and incubated again with the lower aliphatic alcohol.

14. The process according to any one of claims 1, 7, 8, 9 or 10, wherein the product, in addition, is treated at any stage with an organic solvent for removal of lipids.

15. A method for prophylactic or therapeutic treatment of cardiovascular diseases, and after heart surgery, which comprises administering to a patient in need thereof an effective amount of the apolipoproteins as prepared by the process according to any one of claims 1, 7, 8, 9 or 10.

16. The method according to claim 15, wherein the cardiovascular disease is hypercholesterolemia.

* * * * *